(12) United States Patent
Ulbert et al.

(10) Patent No.: US 10,881,724 B2
(45) Date of Patent: *Jan. 5, 2021

(54) METHOD FOR INACTIVATING VIRUSES USING ELECTRON BEAMS

(71) Applicant: Fraunhofer-Gesellschaft zur Förderung der angewandten Forschung e.V., Munich (DE)

(72) Inventors: Sebastian Ulbert, Leipzig (DE); Christiane Wetzel, Dresden (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,410

(22) Filed: Aug. 21, 2018

(65) Prior Publication Data

US 2018/0353594 A1 Dec. 13, 2018

Related U.S. Application Data

(63) Continuation of application No. 14/903,997, filed as application No. PCT/EP2014/066039 on Jul. 25, 2014, now Pat. No. 10,080,795.

(51) Int. Cl.
| | | |
|---|---|---|
| *A61K 39/145* | (2006.01) | |
| *A61K 41/10* | (2020.01) | |
| *A61L 2/00* | (2006.01) | |
| *A61K 39/00* | (2006.01) | |

(52) U.S. Cl.
CPC ............ *A61K 39/145* (2013.01); *A61K 41/10* (2020.01); *A61L 2/007* (2013.01); *A61K 2039/5252* (2013.01); *A61L 2202/21* (2013.01)

(58) Field of Classification Search
None
See application file for complete search history.

(56) References Cited

U.S. PATENT DOCUMENTS

| 8,173,139 B1 | 5/2012 | McReynolds et al. |
| 10,080,795 B2 | 9/2018 | Ulbert et al. |
| 2011/0020393 A1 | 1/2011 | Komiya et al. |

FOREIGN PATENT DOCUMENTS

| CA | 631016 A | 11/1961 |
| DE | 19638925 A1 | 4/1998 |
| GB | 899011 A | 6/1962 |
| JP | H06-113835 A | 4/1994 |

OTHER PUBLICATIONS

Communication pursuant to Article 94(3) EPC for European Patent Application No. 14744820.3 dated Jan. 30, 2019 (5 pages) (No English language translation available).
Stauffer et al., "Advances in the development of inactivated virus vaccines," Recent Pat Antiinfect Drug Discov. 1(3):291-6 (2006).
Kumar et al., "Utilization of 10 MeV RF electron linear accelerator for research and industrial applications," Indian Journal of Pure & Applied Physics. 50(11): 802-4 (2012).
Aikawa et al., "Inactivation of virus contaminating material or instrument—by applying electron beam irradiation at specified exposure rate," WPIDS, AN 1994-172733 [199421] (1 page).
Amanna et al., "Development of a new hydrogen peroxide-based vaccine platform," available in PMC Dec. 1, 2012, published in final edited form as: Nat Med. 18(6):974-9 (2012) (14 pages).
Brahmakshatriya et al., "Preliminary study for evaluation of avian influenza virus inactivation in contaminated poultry products using electron beam irradiation," Avian Pathol. 38(3):245-50 (2009).
Delrue et al., "Assessing the functionality of viral entry-associated domains of porcine reproductive and respiratory syndrome virus during inactivation procedures, a potential tool to optimize inactivated vaccines," Vet Res. 40(6):62 (2009) (15 pages).
Heger, 2. Allgemeine Grundlagen and 4. Industrielle Bestrahlungsanlagen. Technologie der Strahlenchemie von Polymeren. Carl Hanser Verlag Munchen Wien, 25-39, 69-149 1990.
International Preliminary Report on Patentability for International Patent Application No. PCT/EP2014/066039, dated Jan. 26, 2016 (13 pages) (English language translation provided).
International Search Report for International Patent Application No. PCT/EP2014/066039, dated Oct. 13, 2014 (7 pages) (English language translation provided).
Powell et al., Table of Contents. *Vaccine Design: The subunit and adjuvant approach.* Springer Science+Business Media, (42 pages) 1995.
Preuss et al., "Comparison of two different methods for inactivation of viruses in serum," Clin Diagn Lab Immunol. 4(5):504-8 (1997).
Smolko et al., "Virus inactivation studies using ion beams, electron and gamma irradiation," Nucl Instrum Methods Phys Res B. 236:249-253 (2005).

(Continued)

*Primary Examiner* — Benjamin P Blumel
(74) *Attorney, Agent, or Firm* — Clark & Elbing LLP

(57) ABSTRACT

The invention relates to a method for inactivating viruses, characterized in that an immunogenic composition or vaccine comprising at least one virus is irradiated with electron beams, said immunogenic composition or vaccine comprising at least one virus (i) being liquid, in particular being a suspension and (ii) comprising at least one viral immunogen, wherein the antigen structure is preferably substantially retained.

21 Claims, 4 Drawing Sheets

(56) References Cited

OTHER PUBLICATIONS

Figure 1:
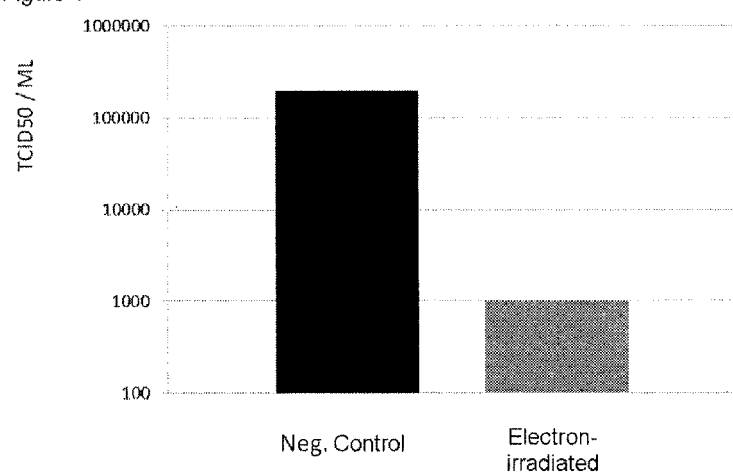

Takahashi et al., "Induction of CD8+ cytotoxic T cells by immunization with purified HIV-1 envelope protein in ISCOMs," Nature. 344(6269):873-5 (1990).
Written Opinion of the International Searching Authority for International Patent Application No. PCT/EP2014/066039, dated Oct. 13, 2014 (11 pages) (English language translation provided).

METHOD FOR INACTIVATING VIRUSES USING ELECTRON BEAMS

The invention relates to a method for inactivating viruses, characterised in that an immunogenic composition or vaccine comprising at least one virus is irradiated with electron beams, said immunogenic composition or vaccine comprising at least one virus (i) being liquid, in particular being a suspension and (ii) comprising at least one viral immunogen.

Through the use of vaccines, many infectious diseases in human and veterinary medicine can be successfully fought. Nevertheless, there is still a major need for vaccine technologies which provide effective and long-lasting protection against infections but which are without risks to the vaccinated individual. This is significant in the preparation of so-called dead vaccines: to inactivate viruses toxic chemicals such as formaldehyde are used which must then be removed again from the vaccine by complex processes. In veterinary medicine, formaldehyde-inactivated vaccines make up the majority of all vaccines and in human medicine they are used, for example, against TBEV, influenza, poliomyelitis or hepatitis A. The use of formaldehyde leads to a chemical alteration (cross-linking) of the viral antigens. This in turn results in an attenuated vaccine efficacy, which must be compensated for by an increased amount of infectious starting material and effect enhancers (adjuvants). A technique to circumvent these problems is a clear unmet need in the vaccine industry.

Studies have shown up to 30%-80% of antigens which are important for a successful vaccination are destroyed by formaldehyde (Amanna et al., Nature Medicine, 18, 2012). These problems are known to the vaccine industry and alternatives are sought. For instance, experiments have been conducted with UV rays, raised temperatures, gamma-rays or peroxides. To date, none of these techniques have progressed beyond the experimental laboratory phase.

It has also been reported that *Salmonella* populations can be reduced by using high-energy electron beams (U.S. Pat. No. 8,173,139B1). However, the extent to which the structure of antigens is impaired was not described therein. Moreover, *Salmonella* are living organisms with their own metabolism. The applicability of electron beams to viruses which, outside of their host cells, have no inherent metabolism, could therefore not be assumed.

In the present invention it has now been found, surprisingly, that viruses could be inactivated with electron beams without destroying viral structural proteins. Surprisingly, therefore, irradiation with electron beams is suitable, particularly for preparing inactivated viral whole particle vaccines.

The viruses are presumably inactivated by destroying the nucleic acid wherein the virus structure, and in particular the antigen structure, is undamaged or barely damaged. The results using the example of the pig pathogenic PRRSV virus are shown in Examples 1 and 2 and FIGS. 1 to 3. In this case, a liquid, namely a suspension of these viruses in buffered aqueous solution, was treated with electron beams. This suspension is immunogenic, and is suitable as a vaccine against PRRSV in pigs.

The results with the influenza A virus are shown in Example 3 and FIGS. 4 and 5. In this case, a liquid, namely a suspension of these viruses in buffered aqueous solution, was treated with electron beams. This suspension is immunogenic, and is suitable as a vaccine against influenza A.

In one embodiment, the present invention relates to a method for inactivating viruses, characterized in that an immunogenic composition or vaccine comprising at least one virus is irradiated with electron beams, said immunogenic composition or vaccine comprising at least one virus (i) being liquid, in particular being a suspension, and (ii) comprising at least one viral immunogen.

In a preferred embodiment, the at least one virus is active prior to irradiation and/or the immunogenic composition or vaccine comprises active viruses. In particular, the concentration of active viruses in the liquid composition or vaccine prior to irradiation, as measured by TCID50 value (50% tissue culture infective dose) per ml of liquid, is at least $10^4$, $10^5$ or $10^6$ per ml.

In another embodiment, the invention relates to a method for inactivating viruses, characterized in that a composition comprising at least one virus is irradiated with electron beams, said composition comprising at least one virus (i) being liquid, in particular being a suspension, and/or (ii) being an immunogenic composition.

The method can be applied to any viruses, particularly enveloped or non-enveloped viruses.

In a preferred embodiment, it is suitable for enveloped viruses, since envelope proteins are suitable antigens for a vaccine reaction. The antigen structure remains intact using the method according to the invention, while the viruses themselves are inactivated (see FIGS. 1, 2 and 3). Surprisingly therefore, using the method according to the invention, in particular an inactivated viral whole particle vaccine can be prepared for enveloped viruses.

In another preferred embodiment, an inactivated viral whole particle vaccine can be prepared for non-enveloped viruses. A suitable antigen for a vaccine reaction in non-enveloped viruses is particularly a capsid protein of the virus.

The following viruses, for example, may be irradiated in accordance with the invention:

enveloped viruses, for example:
double-stranded DNA viruses, for example:
poxvirus (causes smallpox);
herpes viruses (e.g. herpes simplex (HSV) (causes herpes labialis or genitalis); varizella zoster virus (VZV) (causes chickenpox and shingles) Epstein-Barr virus (EBV) (causes glandular fever) cytomegalovirus (CMV) (causes cytomegaly)
human herpes virus 6 7 (causes roseola)
human herpes virus 8 (HHV 8) (causes Kaposi's sarcoma)
hepadnaviruses, for example:
hepatitis B virus (causes hepatitis B)
(+)-strand RNA viruses, for example:
flaviviruses, for example:
hepatitis C virus (causes hepatitis C)
togaviruses, for example:
rubella virus (causes rubella)
coronaviruses (causes gastrointestinal infections, SARS)
(−)-strand RNA viruses, for example:
orthomyxoviruses, for example:
influenza viruses A, B or C (causes influenza) paramyxoviruses, for example:
parainfluenza viruses (causes parainfluenza)
measles virus (causes measles)
mumps virus (causes mumps)
respiratory sincytical virus (RSV)
pneumoviridae, for example the genera:
pneumovirus, metapneumovirus
rhabdoviruses, for example:
rabies virus (causes rabies)
retroviruses, for example:
human immunodeficiency virus (causes AIDS)

HTLV (causes leukemia)
Non-enveloped viruses, for example:
double-stranded DNA viruses, for example:
adenoviruses (causes colds, common colds)
papovaviruses (causes warts)
single-stranded DNA viruses, for example:
parvoviruses, for example:
parvovirus B19 (causes fifth disease)
double-stranded RNA viruses, for example:
rotaviruses (diarrhea)
(+)-strand RNA viruses, for example:
picornaviruses, for example:
polio virus (causes poliomyelitis)
coxsackieviruses
echoviruses
hepatitis A virus (causes hepatitis A)
rhinoviruses (causes colds, common colds)
caliciviruses (causes diarrhea)

In a preferred embodiment, the at least one virus is thus selected from:

(i) an enveloped virus or non-enveloped virus, in particular an enveloped virus, and/or (ii) a dsDNA virus, dsRNA virus, ssRNA virus or ssDNA virus, and/or (iii) a human pathogenic and/or animal pathogenic virus.

In a preferred embodiment, the animal is a mammal, selected in particular from pigs, cows, horses, dogs, cats and sheep.

In a more preferred embodiment, the at least one virus is selected from a human pathogenic and/or animal pathogenic enveloped dsRNA virus, enveloped ss(−)RNA virus or enveloped ss(+)RNA virus.

It has been shown in the examples that the PRRS virus (porcine respiratory and reproductive failure syndrome virus), a single-stranded, positive strand RNA virus of the family Arteriviridae which affects pigs, was inactivated by the method according to the invention such that the virus structure and antigen structure remained largely intact. Therefore, an inactivated viral whole particle vaccine against the PRRS virus could be prepared.

In an even more preferred embodiment, the at least one virus is selected from a human pathogenic and/or animal pathogenic ss(+)RNA virus, very particularly preferably from a virus of the Arteriviridae family, and even more preferably the at least one virus is a porcine reproductive and respiratory syndrome virus (PRRS virus).

In a further preferred embodiment, the at least one virus is selected from an echo virus, HIV virus, rotavirus, pseudorabies virus, parvovirus, porcine parvovirus, H5N1 virus, H1N1 virus, Epstein-Barr virus, mumps virus, influenza A and B virus, the TBEV virus, the IPV virus and the hepatitis A virus.

In a further preferred embodiment, the at least one virus is selected from an animal pathogenic virus, the influenza A and B virus, the TBEV virus, the IPV virus and the hepatitis A virus. Particular preference is given to the influenza A and B virus.

Using the method according to the invention, it is possible to irradiate an immunogenic composition or vaccine comprising one (1) virus, as shown in the examples with PRRSV. It is also possible, however, that the immunogenic composition or vaccine comprises 2, 3, 4, 5, 6, 7, 8, 9, 10 or more different viruses. This may be helpful, for example, for preparing combination vaccines. These two or more different viruses can be variants of the same virus species or viruses of different species, families or genera. In a preferred embodiment, therefore, the immunogenic composition or vaccine comprises (i) one virus or (ii) two or more different viruses. However, it is also possible to prepare a combination vaccine in which two or more viruses are irradiated individually, and are only combined after irradiation.

In the examples, a suspension of PRRSV viruses was irradiated with electrons which were accelerated to less than 300 keV, for example, to 150 keV (see FIGS. 1 to 5). Such electrons are accelerated at low energy.

In a preferred embodiment, the method according to the invention is characterized in that the electron beams are accelerated at low energy or moderate energy, preferably accelerated with an acceleration energy of between 150 keV and 700 keV, more preferably of between 200 keV and 500 keV, even more preferably of between 250 keV and 400 keV.

In this case, it is possible to operate under standard atmospheric pressure or essentially under standard atmospheric pressure and the electron beams can therefore be applied preferably essentially under standard atmospheric pressure. Essentially standard atmospheric pressure is understood to mean 1 bar+/−0.1 bar. The standard atmospheric pressure can be present here, for example, as atmospheric oxygen, nitrogen, or carbon dioxide gas.

As shown in the examples, the PRRSV virus could be inactivated using a dose of 50 kGy, 100 kGy or 200 kGy. Furthermore, it could be shown that the influenza A virus in suspension is completely inactivated at a dose of 200 kGy.

It has been found that a dose of at least 50 kGy is advantageous in order to achieve, as far as possible, complete inactivation of the viruses.

In a preferred embodiment, the method according to the invention is therefore characterized in that the immunogenic composition or vaccine comprising at least one virus is irradiated with an electron beam dose of at least 50 kGy, at least 60 kGy, at least 70 kGy, at least 80 kGy, at least 90 kGy, at least 100 kGy, at least 110 kGy, at least 120 kGy, at least 130 kGy, at least 140 kGy, at least 150 kGy, at least 160 kGy, at least 170 kGy, at least 180 kGy, at least 190 kGy, at least 200 kGy or at least 250 kGy.

Furthermore, it has been found that a dose of 300 kGy or less is advantageous in order to avoid potential damage to the composition.

In a preferred embodiment, the method according to the invention is therefore characterized in that the immunogenic composition or vaccine comprising at least one virus is irradiated with an electron beam dose of at most 300 kGy, at most 250 kGy, at most 200 kGy, at most 190 kGy, at most 180 kGy, at most 170 kGy, at most 160 kGy, at most 150 kGy, at most 140 kGy, at most 130 kGy, at most 120 kGy, at most 110 kGy, at most 100 kGy, at most 90 kGy, at most 80 kGy, at most 70 kGy or at most 60 kGy.

In a preferred embodiment, the electron beam dose is therefore in the range of 50 kGy to 300 kGy. For example, the immunogenic composition or vaccine comprising at least one virus may be irradiated at an electron beam dose of 50 kGy, 60 kGy, 70 kGy, 80 kGy, 90 kGy, 100 kGy, 110 kGy, 120 kGy, 130 kGy, 140 kgy, 150 kGy, 160 kGy, 170 kGy, 180 kGy, 190 kGy, 200 kGy, 210 kGy, 220 kGy, 230 kGy, 230 kGy, 240 kGy, 250 kGy, 260 kGy, 270 kGy, 280 kGy, 290 kGy or 300 kGy.

In a preferred embodiment, the method according to the invention is therefore characterized in that the immunogenic composition or vaccine comprising at least one virus is irradiated with an electron beam dose in the range of 50 kGy to 300 kGy, preferably 50 kGy to 200 kGy, further preferably 50 kGy to 150 kGy, more preferably 50 kGy to 120 kGy, even more preferably 50 kGy to 110 kGy.

In another embodiment of the method according to the invention, the at least one virus is irradiated with an electron beam dose of 1 to 300 kGy, more preferably with an electron beam dose of 1 to 150 kGy, even more preferably with an electron beam dose of 10 to 120 kGy, most preferably with an electron beam dose of 15 to 110 kGy.

In example 1, it was shown that an inactivation by 2.5 logarithmic steps could be achieved by irradiation with electrons by means of the method according to the invention (FIG. 1). The inactivation was determined by measuring the TCID50 value.

In a preferred embodiment, the method according to the invention is therefore characterized in that the activity of the at least one virus after irradiation, preferably measured as a TCID50 value (50% tissue culture infective dose), is less than 5%, preferably less than 1%, more preferably less than 0.1% of the activity prior to irradiation, even more preferably that no activity of the at least one virus is still detectable after irradiation. The TCID50 value can be determined as described in Example 2. The person skilled in the art will therefore select a suitable tissue culture for a particular virus. For the PRRSV virus in Example 2, the TCID50 value was determined in Marc-145 cells. For the influenza A virus in Example 3, the TCID50 value was determined in MDCK cells.

Figure 5:
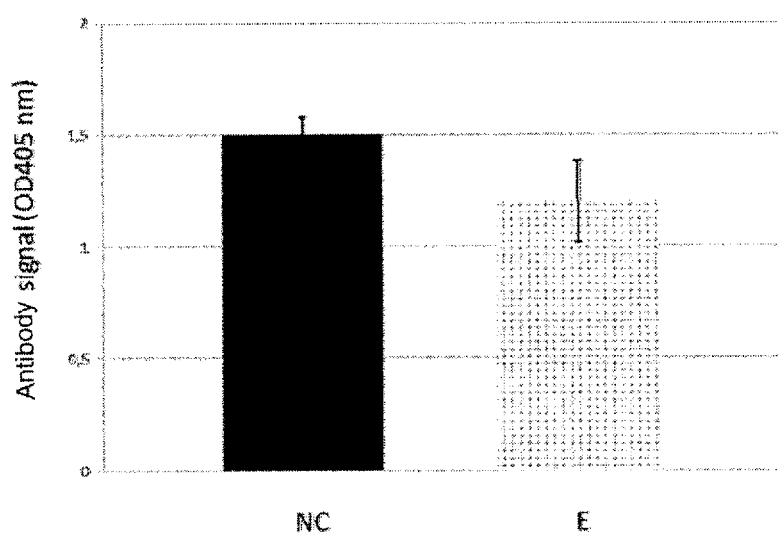

It could be shown in the examples for the enveloped PRRSV virus that the antigen structure was substantially retained under the stated conditions: the binding of a polyclonal serum directed against the non-inactivated virus to the at least one virus of the irradiated composition corresponded to more than 90% of the binding to the non-inactivated virus (see FIG. 1). The antigen structure of influenza viruses which had been treated with an electron beam dose of 200 kGy was also substantially retained (FIG. 5). The binding of a polyclonal serum from an influenza A infected human to the virus irradiated with 200 kGy corresponded to about 80% of the binding to the non-inactivated virus.

In a further embodiment, the method according to the invention is therefore characterized in that the at least one virus is an enveloped virus, and that the antigen structure of the viruses of the immunogenic composition or vaccine was substantially retained after irradiation.

In another further embodiment, the method according to the invention is therefore characterized in that the at least one virus is a non-enveloped virus, and that the antigen structure of the viruses of the immunogenic composition or vaccine was substantially retained after irradiation.

Antigens are substances, especially proteins, capable of binding specifically to antibodies. To act as antigens, the antigens or the epitopes present therein must be chemically and structurally intact. The preservation of the two-dimensional and/or three-dimensional structure of the antigens or the epitopes present therein is frequently necessary for binding to the antibodies. It has now been found, surprisingly, that on irradiation with electron beams the antigen structure of the irradiated viruses is largely retained and thus the irradiated liquid composition may be used as a vaccine to induce a specific immune response in a human or animal, particularly a mammal.

An epitope is a region of an antigen to which an antibody specifically binds.

In a particularly preferred embodiment, the binding of a polyclonal serum directed against the non-inactivated virus to the at least one virus of the irradiated immunogenic composition or vaccine is at least 40%, preferably at least 70%, more preferably at least 80%, even more preferably at least 90% of the binding of the polyclonal serum to the at least one virus of the immunogenic composition or vaccine prior to irradiation.

The binding of the polyclonal serum to the at least one virus of the immunogenic composition or vaccine is preferably determined in this case by ELISA. The determination of the binding by ELISA is preferably carried out as set out in the examples.

ELISA (enzyme-linked immunosorbent assay) refers to an antibody-based detection method which has been well known for decades to those skilled in the art. Using ELISA, substances such as proteins can be detected. What is exploited here is the property of specific antibodies which bind to the substance, the antigen, to be detected. An antibody is first labelled with an enzyme. The reaction catalyzed by the reporter enzyme serves as evidence for the presence of the antigen. A substrate is converted by the enzyme and the reaction product can then be detected, for example by measuring the absorption or chemiluminescence.

In a further embodiment, the method according to the invention is therefore characterized in that the at least one virus is an enveloped virus and that the antigen structure of the viruses of the composition is substantially retained after irradiation.

In another further embodiment, the method according to the invention is therefore characterized in that the at least one virus is a non-enveloped virus and that the antigen structure of the viruses of the composition is substantially retained after irradiation.

In another embodiment, the binding of a polyclonal serum directed against the non-inactivated virus to the at least one virus of the irradiated composition is at least 40%, preferably at least 70%, more preferably at least 80%, even more preferably at least 90% of the binding of the polyclonal serum to the at least one virus of the composition prior to irradiation The binding of the polyclonal serum to the at least one virus of the composition is preferably determined in this case by ELISA. The determination of the binding by ELISA is preferably carried out in this case as set out in the examples.

It is furthermore advantageous for the preparation of immunogenic compositions and vaccines for non-enveloped and enveloped viruses if the virus structure of the viruses is substantially retained after irradiation. This applies particularly if a whole-body vaccine, particularly inactivated whole-body vaccine, is desired. Whole-body vaccines have the advantage that they comprise the various antigens of the virus and can therefore trigger a comprehensive immune response. In the examples, it could be shown for an enveloped virus that the binding of an antibody directed against an antigen of the virus, which is inaccessible to the antibody in the case of intact envelopes of this virus, namely the N-protein of PRRSV, is essentially the same in the irradiated composition and the negative control, while in the peroxide-treated composition an increase in the binding of over 400% was observed.

A whole-body vaccine or whole particle vaccine is a vaccine comprising a virus in which the virus particle structure is substantially retained.

An inactivated whole-body vaccine or whole particle vaccine is a killed vaccine comprising a virus in which the virus structure is substantially retained.

A killed vaccine comprises inactivated or killed viruses or bacteria or constituents of viruses, or bacteria or toxins. These can no longer replicate in the body.

An immunogen according to the present invention is an antigen which is capable of eliciting an immune response due to its immunogenicity.

An immunogenic composition is a composition which is capable of eliciting an immune response in a human or mammal. An immunogenic composition comprises at least one immunogen. In a preferred embodiment, an immunogenic composition is suitable for administration to a human or an animal, and is thus prepared for administration to an animal or human. The composition therefore preferably contains no substances which are not approved or are unsuitable for administration to a human or an animal, in particular, no carcinogenic, highly allergenic or toxic substances.

A vaccine according to the present invention comprises at least one antigen and/or immunogen which, due to its immunogenicity, is capable of eliciting an immune response and is prepared for administration to an animal or human. A vaccine is suitable for administration to a human or animal. A vaccine therefore preferably contains no substances which are not approved or are unsuitable for administration to a human or animal, in particular, no carcinogenic, highly allergenic or toxic substances.

A vaccine directed against a virus preferably provides protection against a viral infection or ameliorates this disease. A vaccine directed against a virus is therefore preferably suitable for the prevention and/or treatment, for example, the alleviation of a viral infection or disease in a human or animal, in particular a mammal.

In a preferred embodiment, the method according to the invention is therefore characterized in that the virus structure of the viruses is substantially retained after irradiation.

In a preferred embodiment, the method according to the invention is therefore characterized in that the at least one virus is an enveloped virus, and that the virus structure of the viruses is substantially retained after irradiation.

In a further preferred embodiment, the method according to the invention is therefore characterized in that the at least one virus is a non-enveloped virus and that the virus structure of the viruses is substantially retained after irradiation.

In the context of the present invention, a virus structure is substantially retained if the binding of an antibody directed against an antigen of the virus, which is inaccessible to the antibody in the case of an intact envelope, to the at least one virus of the composition, particularly immunogenic composition or vaccine, after irradiation is less than 400%, preferably less than 200%, more preferably less than 150%, even more preferably less than 120% of the binding of this antibody to the at least one virus of the composition, particularly immunogenic composition or vaccine, prior to irradiation. This is preferably determined by ELISA, as shown in the examples. It has been shown in FIG. 3, surprisingly, that on irradiation of a liquid immunogenic composition comprising PRRSV viruses, the capsid (N–) protein is not accessible using an antibody against this antigen in an ELISA.

In a further embodiment, therefore, the present invention also relates to the use of a method according to the invention for preparing an inactivated viral whole particle vaccine.

In the method according to the invention electron beams are used. In the industrial generation of electrons—after power-up—the acceleration voltage between the cathode and anode applied in the emission of the electrons to their energy content is given in electron volt eV. The higher this is, the deeper the electrons provided with more energy can penetrate into matter. The radiation power is the product of beam current (amount of electrons generated) and acceleration voltage—specified in kilowatts (kW). At high radiation powers, the energy dose required for triggering chemical reactions by irradiation can be generated and applied in very short times (fractions of a second). Overall, electron beams, despite lower penetration, are particularly advantageous in throughput processes of high amounts of product: physicochemical processes can be initiated and implemented in a technically readily adjustable manner. A major advantage is that the radiation process can be switched on or off virtually at the push of a button (unlike gamma rays for example).

Suitable devices for generating electron beams and devices for carrying out the method are known from the prior art (A. Heger: Technologie der Strahlenchemie von Polymeren [Technology of radiation chemistry of polymers], Carl Hanser Verlag Munich Vienna, 1990. ISBN 3-446-15630-5; Chapter 2: Allgemeine Grunglagen [General principles]; pp. 25-39 and Chapter 4: Industrielle Bestrahlungsanlagen [Industrial irradiation plants]; pp. 69-149; DE 196 389 25 A1).

Electron beams are also advantageous compared to gamma radiation: since conventional gamma sources often only deliver ca. 2 to 6 kGy per hour, higher doses can only be achieved over long time courses, whereas electron beams reach this in a few seconds (high dose rates) and are therefore substantially more productive.

In conventional gamma irradiation in air in commercial service facilities, a long-term concomitant oxidative effect (ozone in air or OH free radicals from water) on the treated material or the reaction process occurs, which often does not, but occasionally does bring about product alterations and product outcomes in the sense desired. In the case of short dose impact by electron beam systems, most of which are also designed to operate under inert atmosphere, such side effects are ruled out over a longer impact time.

The method according to the invention is preferably carried out using a device for generating electron beams which is operated continuously or rapidly pulsed.

In a further preferred embodiment, the method according to the invention is carried out using a device for generating electron beams which provides electrons according to the cold or hot cathode principle.

In a further preferred embodiment, the method according to the invention is carried out using a device for generating electron beams which is embodied as an axial emitter (scanner) or linear broadband emitter.

In a further preferred embodiment of the method according to the invention, the electrons are applied to the composition after discharge through an emission window of the evacuated generating chamber of the device. In this case, the composition, in particular an immunogenic composition or vaccine, is preferably in a container.

In a further preferred embodiment of the method according to the invention, the composition, in particular an immunogenic composition or vaccine, is incorporated statically in the device, or is continuously transported through the electron beam.

Furthermore, the dose rate (beam current/time) can be adjusted. In this case, it is generally to be born in mind—with respect to the desired final applied dose—that a high beam current requires little irradiation time and low beam current requires a long irradiation time. The dose rate is adjusted by a person skilled in the art by considering, for example, the flow rate of the liquid medium in the split tube, as well as the type of emitter.

For example, a dose can be applied in the range of 10 to 300 kGy, particularly 50 to 300 kGy, over a time period of up to 1000 seconds; lower doses of 1 to 25 kGy can be applied preferably over a time period of 0.1 to 100 seconds. Doses above 50 kGy, which are preferred, typically require an application time of 10 seconds to 1000 seconds. Therefore, the application time is preferably 10 seconds to 1000 seconds.

In a further preferred embodiment of the method according to the invention, the dose rate is therefore in the range of 1 kGy/0.1 seconds to 150 kGy/1000 seconds.

In a further preferred embodiment of the method according to the invention, the irradiation time is therefore in the range of 0.1 seconds to 1000 seconds, preferably between 1 second and 100 seconds.

During the irradiation, a temperature increase typically takes place. To avoid denaturing processes, it is therefore advantageous if the temperature rises only slightly.

In a further preferred embodiment of the method according to the invention, the temperature of the composition, in particular an immunogenic composition or vaccine, prior to irradiation is therefore between 1° C. and 40° C., preferably between 5° C. and 37° C., more preferably between 10° C. and 32° C., even more preferably between 15° C. and 30° C.

In another embodiment, it is possible to carry out the irradiation at temperatures of the composition prior to irradiation of less than 1° C., for example, of frozen compositions. In this case, the composition after irradiation can also have a temperature of less than 1° C., or the temperature of the composition after irradiation can be 1° C. or more.

In a further preferred embodiment of the method according to the invention, the temperature increase of the composition, in particular an immunogenic composition or vaccine, after irradiation compared to before irradiation is between 1° C. and 15° C., preferably between 2° C. and 10° C.

In a further preferred embodiment of the method according to the invention, the temperature of the composition, in particular an immunogenic composition or vaccine, after irradiation is therefore between 2° C. and 41° C., preferably between 6° C. and 38° C., more preferably between 11° C. and 33° C., even more preferably between 16° C. and 31° C.

The composition, in particular an immunogenic composition or vaccine comprising at least one virus is liquid. In this case, such a liquid can preferably be in the form of a suspension of viruses in an aqueous solution, as in the examples; however, it may also be a suspension of higher density.

In a further preferred embodiment of the method according to the invention, therefore, the density of the composition, in particular an immunogenic composition or vaccine, is between 0.9 and 2 g/cm$^3$, preferably between 1.0 and 1.8 g/cm$^3$.

In a further preferred embodiment of the method according to the invention, therefore, the composition, in particular an immunogenic composition or vaccine comprising at least one virus, comprises a liquid suspension comprising water, preferably a suspension of the at least one virus in an aqueous solution, wherein the aqueous solution particularly preferably comprises one or more buffer substances. The aqueous buffered solution may be PBS for example. The pH of such a solution is preferably in the range of pH 5.5 to 8.5, more preferably in the range of pH 6.5 to 8.0.

It is possible using the method according to the invention to irradiate an otherwise finished vaccine which already contains suitable auxiliaries and/or adjuvants.

In a further embodiment of the method according to the invention, therefore, the immunogenic composition or vaccine comprises (a) one or more adjuvants and/or (b) pharmaceutically acceptable excipients and/or auxiliaries and/or (c) one or more further immunogens.

In a further preferred embodiment of the method according to the invention, therefore, the immunogenic composition or vaccine consists of at least one virus, in particular (1) one virus and
(a) one or more adjuvants, and/or
(b) pharmaceutically acceptable excipients and/or auxiliaries, such as water or a suitable aqueous solution, particularly preferably comprising one or more buffer substances, and (c) optionally one or more further viruses or immunogens.

In a further embodiment of the method according to the invention, therefore, the composition is a vaccine comprising at least one viral immunogen and optionally comprising (a) one or more adjuvants and/or (b) pharmaceutically acceptable excipients and/or auxiliaries and/or (c) one or more further immunogens.

Suitable excipients and auxiliaries and/or further adjuvants are well known to those skilled in the art. Suitable adjuvants are those that are sufficient to enhance an immune response to an immunogen. Suitable adjuvants are, for example, aluminum salts such as aluminum phosphate or aluminum hydroxide, squalene mixtures (SAF-1), muramyl peptide, saponin derivatives, *mycobacterium* cell wall preparations, monophosphoryl lipid A, mycolic acid derivatives, nonionic block copolymer surfactants, Quil-A, cholera toxin B subunit, polyphosphazene and derivatives and immunostimulating complexes (ISCOMs) such as those described in Takahashi et al. (1990) Nature 344:873-875.

Suitable excipients and auxiliaries are, for example, water or an aqueous solution suitable for administration, particularly preferably comprising one or more buffer substances.

Suitable further immunogens are well known to those skilled in the art and particularly include
(a) organic substances, particularly proteins which may be glycosylated or non-glycosylated, nucleic acids, toxins or sugar molecules, particularly saccharides optionally bound to a support, and
(b) a virus or a living organism, particularly a bacterium, wherein the virus or living organism may be active or inactivated.

Suitable further immunogens are particularly those which induce an immune response to a pathogen or disease factor in the same animal or human as the at least one virus of the composition. For example, if the at least one virus is a human pathogenic virus, further immunogens should be preferably selected such that they trigger an immune response to a human pathogen and/or prevent or ameliorate a human disease.

In the case of lyophilized vaccines, stabilising agents, for example, a polyol such as sucrose or trehalose, may be added as excipients and auxiliaries.

As customary in all immunogenic compositions or vaccines, the immunologically effective dose must be determined empirically. Factors that should be taken into account here are whether an immunogen should be complexed with an adjuvant or carrier molecule or should be covalently bound thereto, the type of administration and the number of immunizing doses which should be given. Such factors are well known in the field of vaccine development and a person skilled in this field can readily determine these factors.

The at least one virus and optionally one or more further immunogens may be present at different concentrations in immunogenic compositions or vaccines of the present invention. The minimum concentration in a vaccine is typically one that is sufficient for its planned use for vaccination, wherein during the irradiation according to the method according to the invention lower concentrations can also be used and a higher concentration can then be adjusted in the finished vaccine or during the irradiation according to the method according to the invention higher concentrations can also be used and a lower concentration can then be adjusted in the finished vaccine. The maximum concentration for the irradiation according to the method according to the invention is typically one in which the at least one virus remains homogeneously suspended during the irradiation and/or optionally one or more further immunogens remain dissolved or homogeneously suspended during the irradiation. The maximum concentration in a vaccine is typically one at which the at least one inactivated virus remains homogeneously suspended and/or optionally one or more further immunogens remain dissolved or homogeneously suspended.

The vaccines of the present invention may be used to protect or to treat a human or an animal, particularly a mammal, by administration, particularly by systemic administration or administration via the mucous membrane. The type of administration may be selected by those skilled in the art and includes, for example, injection via the intramuscular, intraperitoneal, intradermal or subcutaneous route or the administration via the mucous membrane of the oral, respiratory or genitourinary tract.

The preparation of vaccines is described in general in Vaccine Design ("The subunit and adjuvant approach", eds. Powell M. F. & Newman M J.) (1995) Plenum Press New York).

Alternatively, however, it is also possible in accordance with the invention to initially irradiate a composition, particularly an immunogenic composition, comprising at least one virus and subsequently optionally to add suitable auxiliaries and/or adjuvants. Further immunogens for preparing combination vaccines can also be added.

In a further embodiment, the invention therefore relates to a method for preparing a vaccine comprising at least one viral immunogen, in particular a vaccine comprising a viral whole particle vaccine, characterized in that:

(a) the method according to the invention is carried out as described above, (b1) one or more adjuvants are added to the composition, particularly an immunogenic composition, comprising at least one virus, and/or (b2) one or more pharmaceutically acceptable excipients and/or auxiliaries are optionally added to the composition, particularly an immunogenic composition, comprising at least one virus, and/or (b3) one or more further immunogens are optionally added to the composition, particularly an immunogenic composition, comprising at least one virus, wherein the steps (a) to (b3) are carried out in any sequence.

To be suitable for application to an animal or a human, and to ensure secure transport and application at a defined dose, such a vaccine is usually sterile and filled into a suitable container. Such a container may comprise multiple doses or single doses.

In a further preferred embodiment, the method according to the invention for preparing a vaccine is characterized in that the following further steps are carried out:

(c) sterilizing the immunogenic composition, and/or (d) filling the immunogenic composition in a container, wherein steps (a) to (d) may be carried out in any sequence, and following steps (a) to (d) the vaccine is optionally dried, freeze-dried or frozen.

In a further embodiment of the method according to the invention, therefore, the composition comprising at least one virus is in addition (c) sterilised, and/or (d) filled in a container, wherein steps (a) to (d) may be carried out in any sequence, and then the vaccine is optionally dried, freeze-dried or frozen.

The immunogenic compositions and vaccines obtained by the method according to the invention are clearly superior to the compositions of the prior art since they do not comprise any residues of chemical inactivating substances (such as formaldehyde) and/or and are characterized by the intact antigen structure of the virus with simultaneous inactivation of the at least one virus. This is particularly the case in a whole particle vaccine and/or killed vaccine.

The invention therefore further relates to an immunogenic composition or vaccine, preferably vaccine, particularly preferably comprising an inactivated viral whole particle vaccine, which can be prepared by the method according to the invention.

In a further embodiment, the invention relates to an immunogenic composition or vaccine, preferably vaccine, comprising an inactivated viral whole particle vaccine for an enveloped or non-enveloped virus, preferably enveloped virus, characterised in that (a) the activity of the virus in the immunogenic composition or vaccine is less than 10%, preferably less than 1%, more preferably less than 0.1% of the activity of the same number of non-inactivated viruses, and (b) the antigen structure of the inactivated viruses in the immunogenic composition or vaccine is substantially the same compared to the same number of non-inactivated viruses.

In a preferred embodiment of an immunogenic composition or vaccine according to the invention, the virus structure of the inactivated viruses is substantially the same compared to the same number of non-inactivated viruses.

In a further preferred embodiment, the immunogenic composition or vaccine according to the invention has been irradiated with an electron beam as described above.

In a further preferred embodiment, the immunogenic composition or vaccine according to the invention has been irradiated with an electron beam dose of 50 kGy to 300 kGy, preferably 50 kGy to 200 kGy, further preferably 50 kGy to 150 kGy, more preferably 50 kGy to 120 kGy, even more preferably 50 to 110 kGy. This dose allows effective inactivation of a virus, wherein at the same time the virus structure and antibody structure of an enveloped or non-enveloped virus, preferably enveloped virus, is retained.

In a further preferred embodiment, no activity of the at least one virus is still detectable in the composition, in particular an immunogenic composition or vaccine. This is particularly important for a dead vaccine and/or inactivated viral whole body vaccine.

In a further embodiment, the invention relates to an immunogenic composition, preferably vaccine, according to the invention for use as a vaccine, particularly for the prevention or treatment, particularly amelioration of viral infections or disorders which are caused by the virus.

In a further embodiment, the invention relates to the use of electron beams for inactivating viruses in an immunogenic composition or vaccine comprising at least one virus, said immunogenic composition or vaccine (i) being liquid, in particular being a suspension and (ii) comprising at least one viral immunogen.

In a further embodiment, the invention relates to the use of electron beams for inactivating viruses in liquid compositions, preferably liquid immunogenic compositions or vaccines, more preferably vaccines.

In a further embodiment, the invention relates to the use of electron beams for preparing an inactivated viral whole particle vaccine.

In a preferred embodiment of the use according to the invention, the electron beams are accelerated at low energy or moderate energy, preferably accelerated with an acceleration energy of between 150 keV and 700 keV, more preferably of between 200 keV and 500 keV, even more preferably of between 250 keV and 400 keV and/or are applied essentially under standard atmospheric pressure, wherein the standard atmospheric pressure is present as atmospheric oxygen, nitrogen or carbon dioxide gas.

In a preferred embodiment of the use according to the invention, the electron beam dose is in the range of 50 kGy to 300 kGy, preferably 50 kGy to 200 kGy, further preferably 50 kGy to 150 kGy, more preferably 50 kGy to 120 kGy, even more preferably 50 kGy to 110 kGy.

In a further embodiment, the invention relates to the use of a device for generating electron beams for inactivating viruses in liquid compositions, preferably liquid immunogenic compositions, more preferably vaccines, particularly liquid vaccines.

In a further embodiment, the invention relates to the use of a device for generating electron beams for preparing an inactivated viral whole particle vaccine.

In a preferred embodiment of the uses according to the invention, the device is suitable for emitting electron beams accelerated at low energy or moderate energy, preferably suitable for emitting electron beams accelerated at an acceleration energy of between 150 keV and 700 keV, more preferably suitable for emitting electron beams accelerated at an acceleration energy of between 200 keV and 500 keV, even more preferably suitable for emitting electron beams accelerated at an acceleration energy of between 250 keV and 400 keV.

In a further preferred embodiment of the uses according to the invention, the device is suitable for applying electron beams essentially under standard atmospheric pressure.

In a further preferred embodiment of the uses according to the invention, the device is suitable for emitting an electron beam dose of 50 kGy to 300 kGy, preferably 50 kGy to 200 kGy, further preferably 50 kGy to 150 kGy, more preferably 50 kGy to 120 kGy, even more preferably 50 kGy to 110 kGy.

In a further preferred embodiment of the uses according to the invention, the device is suitable for emitting an electron beam dose of 1 to 300 kGy, more preferably an electron beam dose of 1 to 150 kGy, even more preferably an electron beam dose of 10 to 120 kGy, most preferably an electron beam dose of 15 kGy to 110 kGy.

The preferred embodiments of the method according invention also apply to the uses and immunogenic compositions and vaccines according to the invention, as far as applicable.

FIGURES

FIG. 1: shows the PRRS virus activity after treatment with the electron beam (gray) and without irradiation (black). Stated values are TCID50 per ml of virus solution. Dose: 100 kGy.

Figure 2:
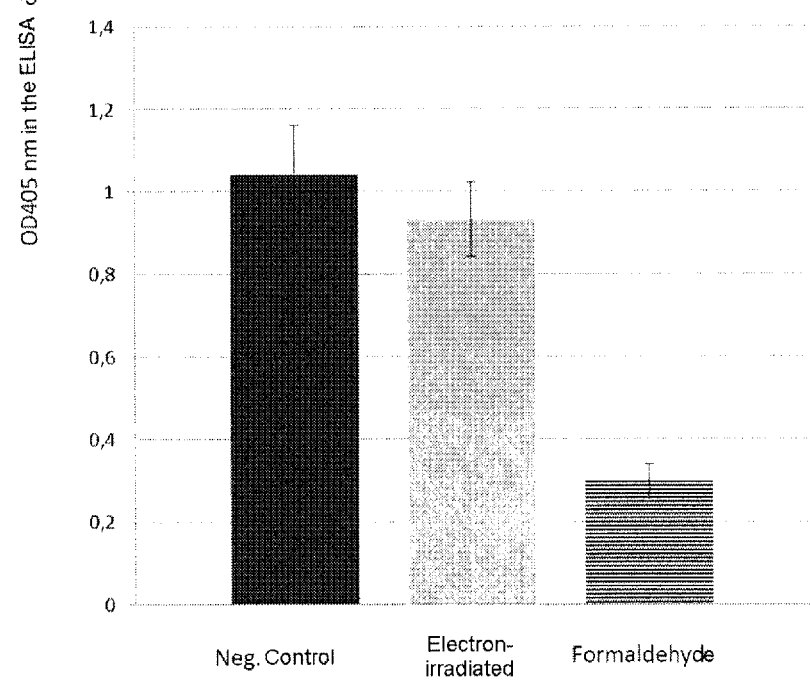

FIG. 2: shows the results for the antigen integrity after treatment. PRRS viruses were treated with an electron beam (gray), formaldehyde (stripes) or untreated (black). The integrity of the antigens was determined via incubation using a polyclonal serum from a PRRSV infected pig. Stated values are OD (optical density) in the ELISA. Dose: 100 kGy.

Figure 3:
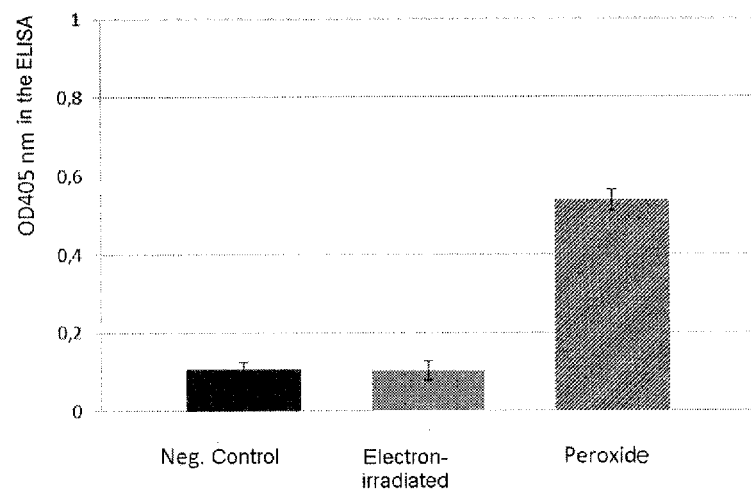

FIG. 3: shows the results for the integrity of the virus envelope after treatment. PRRS viruses were treated with an electron beam (gray), peroxide (stripes) or untreated (black). The integrity of the virus envelope was analyzed using an antibody against the capsid (N–) protein of PRRSV. Stated values are OD in the ELISA. Dose: 100 kGy.

Figure 4:
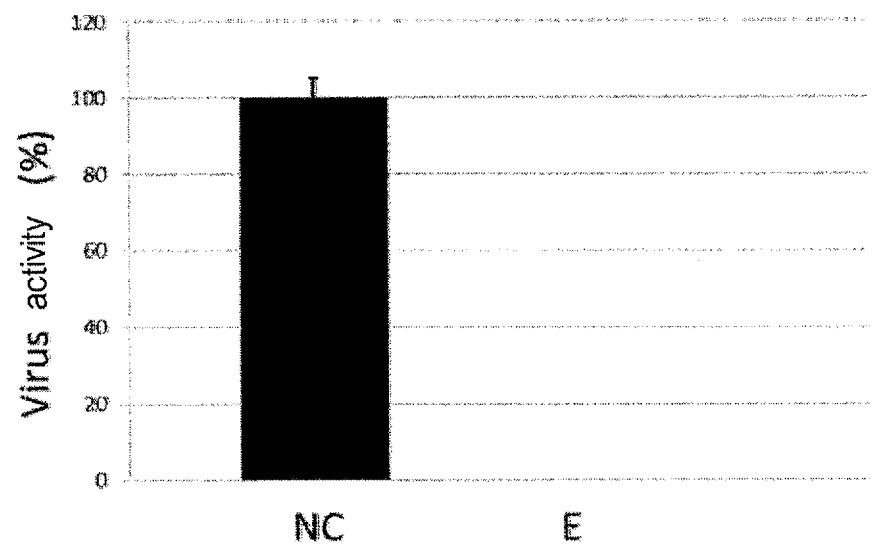

FIG. 4: H3N8 viruses were treated with low-energy electrons of 200 kGy (E) or 0 kGy (NC) and their activity measured by TCID50 determination.

FIG. 5: the integrity of the antigens was determined by incubation with a serum from an influenza-positive human. Values are absorption signals in an ELISA test. E: H3N8 viruses treated with an electron beam dose of 200 kGy; NC: H3N8 viruses treated with 0 kGy (control).

EXAMPLE 1

Summary of the Experiments

The experiments were carried out, for example, using the PRRS virus (porcine respiratory and reproductive failure syndrome virus). This virus is a single-stranded, positive strand RNA virus of the Arteriviridae family. The virus affects pigs and causes annual losses in the pig industry in the billions.

PRRSV in 100 µL of liquid medium was conducted through the electron beam and irradiated with 100 kGy. The amount of virus used was $2*10^4$ TCID50 per batch. Subsequently, the activity of the pathogens and the conservation of their antigens was investigated.

For the activity determination, the viruses (and the untreated controls) were added to Marc145 cells and the TCID50 value determined three days later. The irradiation resulted in a reduction of the activity by 2.5 logarithmic steps compared to the control (FIG. 1). The quality of the antigens was investigated by measurements using antibodies. For this purpose, sera from pigs which had been infected with a vaccine strain of PRRSV were investigated. Immunisation with a live virus leads to a comprehensive humoral immune response against the antigens in their original undamaged state. Therefore, the extent of binding of polyclonal antibodies from an animal thus immunized to an antigen is a direct indicator of the integrity of the antigen. FIG. 2 clearly shows that the binding properties of the pig serum to the PRRSV viruses have hardly changed as a result of irradiating the viruses. Consequently, almost all antigens are still in their original undamaged state, although the virus was inactivated by 2.5 logarithmic steps. PRRS viruses were also inactivated with formaldehyde for comparison. This process resulted in a significant decrease in the ELISA signal and therefore a clear destruction of the antigens.

It was also investigated to what extent the inactivation process affects the virus structure. This was measured using an antibody against the capsid protein (N-protein) of the PRRSV. This protein is protected by the intact virus envelope and is not accessible by the antibody. Therefore, a signal indicates a damaged virus envelope. As FIG. 3 shows, the virus envelope remains intact after irradiation while the peroxide inactivation according to Amanna et al. (supra) leads to significant damage to the structure. These data indicate that during the electron irradiation the inactivation is presumably due mainly to the destruction of the nucleic acids while the antigens and the virus structure remain largely unaltered.

The method described, therefore, is suitable for preparing inactivated virus particles, e.g. for the preparation of vaccines, where it has clear advantages over formaldehyde: the antigens are far better preserved and the addition of toxic chemicals can be dispensed with.

EXAMPLE 2

Materials and Methods

Virus Culture, Inactivation and Irradiation

Cell cultures of Marc-145 cells were infected with PRRSV (DV vaccine strain). After three days, the supernatants were removed and centrifuged at 4000×g at 4° C. for 15 minutes. The supernatants thus clarified were layered on a 15% sucrose cushion and ultracentrifuged at 100 000×g for three hours. This supernatant was removed and the pellet resuspended in sterile PBS (phosphate-buffered saline, pH 7.4). After determining the infectivity, the virus suspension was adjusted to a concentration of $2*10^5$ TCID50/mL. Each 100 μL of this solution was added to 6-well plates (which had been previously coated with 0.5% agarose) and irradiated at 50, 100 and 200 kGy. Negative controls were treated identically up to the irradiation.

After irradiation, the virus-containing solution was removed and was further used in TCID50 and antigen measurements. PRRSV was inactivated with 0.3% formaldehyde for 22 hours. The formaldehyde was then removed again from the virus suspension by dialysis. The inactivation by peroxide was carried out according to Amanna et al. (supra) in 3% $H_2O_2$ for 22 hours, followed by dialysis.

TCID50 Measurements

In order to investigate the activity of the irradiated viruses, serial dilutions (each in steps of 1:10) of the virus suspensions in Marc-145 cells were added to 96-well plates. Three days later, the cytopathic effect (CPE) was determined. The TCID50 corresponds to the dilution at which 50% of the infected cell culture wells still have a CPE.

Antigen Measurements 1.5 μL of the virus suspension (irradiated and control samples) were incubated overnight at 4° C. in 96-well microtitre plates. The next day, an ELISA (enzyme-linked immunosorbent assay) was carried out according to a standard protocol. To detect the antigens, serum from a PRRSV-infected (DV vaccine strain) pig was used (dilution 1:100). For the detection, a secondary anti-pig IgG antibody was used (conjugated with horseradish peroxidase, Zymed) at a 1:5000 dilution.

Irradiation with Electrons

The composition comprising PRRSV viruses was thinly applied to a large agarose surface for the irradiation. In detail, the following was carried out:

1.) Preparation of 0.5% agarose gels in PBS,
2.) Pouring the gels into gel pouring apparatus for 1 mm layer thickness,
3.) Cutting out the gels in circular form of 3.5 cm diameter,
4.) Drying the gels (ca. 14 h under continuous sterile work bench) in petri dishes (3.5 cm diameter), the dosimetry negative controls were then dried with a dosimeter foil already inserted,
5.) Dispensing 100 μL of virus suspension (pure PBS for dosimetry negative controls, ca 15 min. exposure)
6.) Packaging with PET/PE film,
7.) Irradiation under the conditions stated below.

The irradiation was carried out by quasi-stationary irradiation of 100 ml of medium in each case in air.

A continuously operating electron beam emitter (Navarone type, manufacturer: COMET) was used. The electrons were accelerated to 150 keV, the beam current was 5 mA. Distance in air between the composition comprising PRRSV viruses and the electron emission window: 45 mm.

The application of energy doses of 50, 100 and 200 kGy was performed in single steps of 25 kGy each (corresponding to 2, 4 or 8 cycles of the samples or linear passages each of 115 mm/sec). The target doses could be achieved under standard atmospheric pressure air with an accuracy of ca. 10%.

The documentation of the applied dose was performed spectrometrically using pararosaniline cyanide dosimeter films and the Risöscan system at a measuring wavelength of 554 nm. For irradiation at 100 kGy, the dosimeter film was changed after 50 kGy since the dosimeter type mentioned has a measuring range of up to a maximum of 80 kGy. For the target dose of 200 kGy, the dosimeter film was correspondingly changed after 50, 100 and 150 kGy.

The blank sample showed no dose input, i.e. the applied dose is due exclusively to the electron beam treatment and the contact with PBS and the agarose gels did not cause any change to the dosimeter strips.

EXAMPLE 3

Irradiation of Influenza Viruses

Influenza A viruses (equine influenza H3N8, strain A/equine 2/Miami/1/63) were propagated in MDCK cells and concentrated by ultracentrifugation analogously to PRRS viruses (Examples 1 and 2).

The irradiation with electron beams was also conducted analogously to Examples 1 and 2 but at a dose of 0 kGy (control) and 200 kGy.

The activity measurements were performed via a TCID50 endpoint determination. The antigens were assayed in the ELISA format using the serum of an influenza A-infected human.

As with PRRSV, inactivation of the influenza viruses is shown. At a dose of 200 kGy, no active viruses were still detectable in the cell culture (FIG. 4). Nevertheless, antigens are still present and largely unchanged (FIG. 5).

The invention claimed is:

1. A method for inactivating viruses, characterized in that an immunogenic composition or vaccine comprising at least one virus is irradiated with electron beams, said immunogenic composition or vaccine comprising at least one virus
   (i) being liquid, and
   (ii) comprising at least one viral immunogen,
   wherein said immunogenic composition or vaccine comprising at least one virus is irradiated with an electron beam dose in the range of between 15 and 110 kGy and the irradiation time is in the range of between 1 second and 100 seconds, and wherein the irradiation is carried out using a device for generating electron beams which is operated continuously.

2. The method as claimed in claim 1, characterized in that the at least one virus is selected from the group consisting of:
   (i) an enveloped virus or non-enveloped virus,
   (ii) a dsDNA virus, dsRNA virus, ssRNA virus or ssDNA virus, and
   (iii) a human pathogenic and/or animal pathogenic virus.

3. The method as claimed in claim 1, characterized in that the vaccine or immunogenic composition (i) comprises one virus or (ii) two or more different viruses.

4. The method as claimed in claim 1, characterized in that the electron beams are accelerated at low energy or moderate energy, and/or are applied under pressure of 1 bar+/−0.1 bar.

5. The method as claimed in claim 1, characterized in that the activity of the at least one virus after irradiation is less than 5% of the activity prior to irradiation.

6. The method as claimed in claim 1, characterized in that the at least one virus is an enveloped virus.

7. The method as claimed in claim 1, characterized in that
(a) the irradiation is carried out using a device for generating electron beams,
  (i) which provides electrons according to the cold or hot cathode principle, and/or
  (ii) which is embodied as an axial emitter (scanner) or linear broadband emitter, and/or
  (iii) the electrons, after discharge through an emission window of an evacuated generating chamber of the device, are applied to the immunogenic composition or vaccine, and/or
  (iv) the immunogenic composition or vaccine is incorporated statically in the device, or is continuously transported through the electron beam,
and/or
(b) the temperature of the immunogenic composition or vaccine prior to irradiation is between 1° C. and 40° C., and/or
(c) the temperature increase of the immunogenic composition or vaccine after irradiation compared to before irradiation is between 1 K and 15 K, and/or
(d) the temperature of the immunogenic composition or vaccine after irradiation is between 2° C. and 41° C., and/or
(e) the density of the immunogenic composition or vaccine is between 0.9 and 2 g/cm$^3$, and/or
(f) the immunogenic composition or vaccine comprising at least one virus is a liquid suspension comprising water.

8. The method as claimed in claim 1, characterized in that the immunogenic composition or vaccine comprises
(a) one or more adjuvants, and/or
(b) one or more pharmaceutically acceptable excipients and/or auxiliaries,
and/or
(c) one or more further immunogens.

9. The method as claimed in claim 8, characterized in that the one or more further immunogens is
(a) an organic substance, a protein which is glycosylated or non-glycosylated, a nucleic acid, a toxin, or a sugar molecule, or
(b) a virus or a living organism, wherein the virus or living organism is active or inactivated.

10. A method for preparing a vaccine comprising at least one viral immunogen, characterized in that:
(a) an immunogenic composition comprising at least one virus is irradiated with electron beams, said immunogenic composition comprising at least one virus (i) being liquid, and (ii) comprising at least one viral immunogen,
wherein said immunogenic composition or vaccine comprising at least one virus is irradiated with an electron beam dose in the range of between 15 and 110 kGy and the irradiation time is in the range of between 1 second and 100 seconds, and wherein the irradiation is carried out using a device for generating electron beams which is operated continuously,
(b1) one or more adjuvants are optionally added to the immunogenic composition comprising at least one virus, and/or
(b2) one or more pharmaceutically acceptable excipients and/or auxiliaries are optionally added to the immunogenic composition comprising at least one virus, and/or
(b3) one or more further immunogens are optionally added to the immunogenic composition comprising at least one virus,
wherein the steps (a) to (b3) are carried out in any sequence.

11. The method for preparing a vaccine as claimed in claim 10, characterized in that the following further steps are carried out:
(c) sterilizing the immunogenic composition, and/or
(d) filling the immunogenic composition into a container,
wherein steps (a) to (d) are carried out in any sequence,
and following steps (a) to (d) the vaccine is optionally dried, freeze-dried, or frozen.

12. The method of claim 1, wherein a dose rate is in the range of 0.15 kGy/sec to 10 kGy/sec.

13. The method of claim 1, characterized in that the immunogenic composition or vaccine comprising at least one virus is irradiated with an electron beam dose of at most 100 kGy.

14. The method of claim 1, characterized in that the immunogenic composition or vaccine comprising at least one virus is irradiated with an electron beam dose of at most 90 kGy.

15. The method of claim 1, characterized in that the immunogenic composition or vaccine comprising at least one virus is irradiated with an electron beam dose of at most 80 kGy.

16. The method of claim 1, characterized in that the immunogenic composition or vaccine comprising at least one virus is irradiated with an electron beam dose of at most 70 kGy.

17. The method of claim 1, characterized in that the immunogenic composition or vaccine comprising at least one virus is irradiated with an electron beam dose of at most 60 kGy.

18. The method of claim 1, wherein the irradiation time is between 1 sec to 10 sec.

19. The method of claim 1, wherein the electron beams are accelerated with an acceleration energy of between 150 keV and 700 keV.

20. The method of claim 1, wherein the electron beams are accelerated with an acceleration energy of between 200 keV and 500 keV.

21. The method of claim 1, wherein the electron beams are accelerated with an acceleration energy of between 250 keV and 400 keV.

* * * * *